United States Patent [19]

Galiatsatos et al.

[11] Patent Number: 5,676,972
[45] Date of Patent: Oct. 14, 1997

[54] TIME-RELEASE DELIVERY MATRIX COMPOSITION AND CORRESPONDING CONTROLLED-RELEASE COMPOSITIONS

[75] Inventors: Vassilios Galiatsatos, Stow, Ohio; Lubica Alabakovska, Cary, N.C.

[73] Assignee: The University of Akron, Akron, Ohio

[21] Appl. No.: 391,420

[22] Filed: Feb. 16, 1995

[51] Int. Cl.$^6$ ..................... A61K 9/14
[52] U.S. Cl. ............ 424/486; 424/497; 424/473; 424/469
[58] Field of Search ............... 424/486, 497, 424/473, 469; 71/93

[56] References Cited

U.S. PATENT DOCUMENTS

| | | | |
|---|---|---|---|
| 3,576,760 | 4/1971 | Gould | 252/403 |
| 3,963,685 | 6/1976 | Abrahams | 252/230 |
| 4,177,056 | 12/1979 | Mueller et al. | 71/93 |
| 4,272,518 | 6/1981 | Moro et al. | 424/81 |
| 4,563,184 | 1/1986 | Korol | 604/368 |
| 4,666,702 | 5/1987 | Junginger | 424/497 |
| 4,747,845 | 5/1988 | Korol | 604/368 |
| 4,857,334 | 8/1989 | Korol et al. | 424/445 |
| 4,997,656 | 3/1991 | Shikinami et al. | 424/448 |

*Primary Examiner*—Thurman K. Page
*Assistant Examiner*—William E. Benston, Jr.
*Attorney, Agent, or Firm*—Renner, Kenner, Greive, Bobak, Taylor & Weber

[57] ABSTRACT

A composition is provided for use as a matrix for controlled-release compositions. Such compositions utilize an active ingredient dispersed in a matrix. Active ingredients include, for example, pharmaceuticals and agricultural agents. The matrix is a blend of a poly(hydroxyethyl) methacrylate, polyethylene glycol and a time-release extending agent which is a low molecular weight polymer having hydrophilic and hydrophobic side groups, such as diblock or triblock poly(ethylene oxide propyleneoxide).

21 Claims, No Drawings

TIME-RELEASE DELIVERY MATRIX COMPOSITION AND CORRESPONDING CONTROLLED-RELEASE COMPOSITIONS

The mechanism is understood to be a result of polymer chain relaxation in which swelling controls the rate of polymer relaxation and influences the diffusion of solutes through the gel. One polymer matrix resin which has been investigated in the prior art includes generally polyhydroxyalkyl acrylates or methacrylates, and more particularly, poly(2-hydroxyethyl methacrylate) or "PHEMA."

U.S. Pat. No. 4,563,184 to Korol relates to the use as a wound dressing of this polymer with poly(ethylene glycol) ("PEG") and a plasticizer which is dimethyl sulfoxide ("DMSO"). A related patent, U.S. Pat. No. 4,797,845, also to Korol, relates to a similar polyhydroxyalkyl methacrylate used in conjunction with poly(ethylene glycol) and DMSO as a time-extended delivery system. Finally, U.S. Pat. No. 4,857,334, to Korol et al., relates to a similar polymer matrix incorporating epidermal growth factor as a wound dressing.

The inventions of all three of the foregoing patents have the disadvantage of incorporating DMSO as a critical element. DMSO is currently on the Federal Food and Drug Administration's list of non-approved substances.

Other related patents include U.S. Pat. No. 3,576,760 to Gould; U.S. Pat. No. 3,963,685 to Abrahams; and U.S. Pat. No. 4,272,518 to Moro et al. However, the prior art does not address the use of a blend-composition as a time-release matrix which unexpectedly provides optimized controlled-release characteristics.

OBJECT OF THE INVENTION

It is an object of the invention to provide a novel polymeric matrix composition which utilizes a time-release extending agent to optimize the drug-delivery characteristics of the matrix composition. Optionally, the matrix further eliminates the use of a DMSO solvent.

Thus, the present invention provides a time-release delivery matrix composition comprising a hydrophilic polyhydroxyalkyl acrylate or methacrylate blended with a polyalkylene glycol, and a copolymer time-release extending agent having hydrophilic and hydrophobic groups. This agent is preferably a low molecular weight block copolymer such as a diblock copolymer having a hydrophilic and hydrophobic side or a triblock copolymer of such units. Preferably, the matrix resin comprises a blend of from about 10 to about 90 percent PHEMA, and from about 5 to about 85 percent PEG (polyethylene glycol), and from 5 to about 30 percent poly(ethylene oxide)/poly(propylene oxide) copolymer preferably having 25 to 80 percent poly (propylene oxide) repeat units.

DETAILED DESCRIPTION OF THE INVENTION

The present invention generally relates to a controlled-release composition comprising an active ingredient dispersed in a matrix composition wherein the matrix composition is a biologically compatible, nontoxic, hydrophilic, water-soluble blend composition.

The matrix composition is a blend composition incorporating a hydrophilic polyhydroxyalkyl acrylate or methacrylate, a polyalkylene glycol, and one or more time-release extending agents having both hydrophilic and hydrophobic groups.

A suitable polyhydroalkyl acrylate or methacrylate has the formula I:

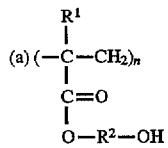

wherein $R^1$ is alkyl having 1–4 carbon atoms, preferably $C_1$ to $C_2$ alkyl and most preferably methyl, and $R^2$ is alkyl having 1–8 carbon atoms, preferably 1–4 carbon atoms and most preferably is ethyl. Thus, poly(hydroxyethyl) methacrylate "poly(HEMA)" is particularly preferred. The number average molecular weight should be 500,000–2,000,000 and preferably 750,000–1,500,000.

Suitable amounts of the acrylate (a) are from about 10 to about 90 percent, preferably from about 20 to about 80 percent and most preferably from about 30 to about 70 percent, this percent being weight percent based on the weight of the blended components of the matrix composition (i.e., a+b+c).

The acrylate or methacrylate is blended with a hydrophilic glycol such as polyethylene glycol ("PEG") PEG has the formula II:

(b) HO—(CH$_2$CH$_2$O)$_n$—H      II wherein the number average molecular weight is from about 200 to about 1,000, preferably from about 300 to about 600, and most preferably from about 300 to about 500. Suitable amounts range from about 5 to about 85 percent, preferably from about 15 to about 75 percent and most preferably from about 20 to about 60 percent. This amount is a weight percent based on a +b+c.

The composition further includes a time-release extending agent which is a relatively low molecular weight compound having both hydrophobic and hydrophilic side groups. For example, the agent can be a diblock or triblock material having one of the formulas III:

(c) HO—(AB)—H      III

HO—(ABA)—H      III'

HO—(BAB)—H      III"

wherein A is preferably (CH$_2$CH$_2$O) and B is preferably (CH(CH$_3$)CH$_2$O).

Suitable number average molecular weights for this component range from 500 to about 10,000, preferably from about 1,000 to about 5,000, and most preferably from about 2,000 to about 4,000. A particularly suitable polymer has the formula:

H—(CH$_2$CH$_2$O)$_a$—(CH—CH$_2$O)$_b$—(CH$_2$CH$_2$O)$_c$—H
                                |
                                CH$_3$ wherein the polypropylene oxide is present at from about 40 to about 70 percent, preferably from about 50 to about 60 percent and most preferably around 55 percent based on the weight of the polyalkylene oxide copolymer. Suitable amounts of the copolymer are from about 0.5 to about 85 percent, preferably from about 5 to about 40 percent, and most preferably from about 5 to about 30 percent by weight based on the total weight of the components (a)+(b)+(c).

The matrix is blended with an active ingredient which can be any controlled-release agent for pharmaceutical or agricultural use (including, for example, insecticides, pesticides, herbicides and fertilizers). By "active ingredient" it is meant an ingredient that is administered to a subject with the intention of causing a desired change. Suitable pharmaceuticals include those which are optimally administered as a controlled-dosage drug meaning that the drug is administered or released into the blood stream or other biologically active site in a controlled relationship of dose to time.

One example of a suitable drug is diltiazem hydrochloride ("DTZ") which is a calcium channel blocking agent used in the treatment of angina and hypertension. The formula is given below:

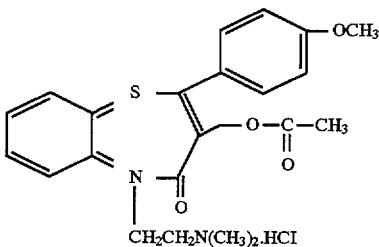

DTZ is incorporated into the matrix in amounts from about 5 to about 40 pph and preferably from about 10 to about 30 pph based on 100 parts by weight of the matrix resin.

The composition is generally made by blending, such as by blending any liquid and solid components. Solid components are optimally first ground to particulate form having a particle size of from about 5 to about 500μ. Alternatively, the active ingredient could be dissolved in a solvent. Preferably, the blend composition utilizes only approved ingredients, for example, the system is substantially free of DMSO. Further the pH of the system will effect the release characteristics for DTZ and is preferably in the range of 3 to 9.

The blended ingredients are then subjected to low heat such as a 40° C. water bath for several hours to permit gelation to occur. Additional blending may be performed before dissolution testing.

The invention will be better understood by reference to the following examples which serve to illustrate but not limit the invention.

EXAMPLES

Polymer blends containing PHEMA and PEG, two hydrophilic macromolecules, and P(EO-PO), a copolymer with a hydrophobic block linking the two hydrophilic blocks, were studied as potential controlled-release devices. DTZ was selected as the water-soluble drug for immobilization in the gels. Drug release profiles were obtained for blends of various compositions to study the effect of the matrix components on the rate of DTZ release. The swelling characteristics of non-drug loaded gels were analyzed and the thermal properties of the unswollen gels were measured using DSC.

Materials

The materials used in the examples are described in this section. Poly(2-hydroxyethyl methacrylate) ("PHEMA") was used either as received in the form of large, glassy pellets, or ground to a powder using a porcelain mortar and pestle. The poly(ethylene glycol) ("PEG") used was quoted to have an "average molecular weight of 400" and was a liquid at room temperature. The poly(ethylene oxide-propylene oxide) used ("P(EO-PO)") was in liquid form with a molecular weight of 2917 g/mol. It had an ethylene oxide to propylene oxide ratio of 0.8:1 or 45 percent by weight ethylene oxide. If used, pharmaceutical-grade dimethyl sulfoxide ("DMSO") was used as received. A dry buffer salt containing monobasic potassium phosphate and disodium phosphate was diluted with distilled water at an amount of 5.58 g of salt to make 1L of a pH 7.4 buffer solution, the release medium. Clear gelatin capsules were used which hold up to 1 g of material. Dialtiazem hydrochloride ("DTZ") was used as an active ingredient. It is sold under the trade name Cardizem (MDL 20, 307A) by Marion Merrell Dow. DTZ is a white crystalline powder with a molecular weight of 450,988 g/mol. It has a pKa of 7.7 and a solubility of 56.6 g of DTZ/100 ml of water. It was stored at room temperature in a tight container.

Sample Preparation

Capsules for dissolution testing were prepared by blending the polymers and drug in desired proportions. The solid materials, PHEMA and DTZ, were measured first into a 4 in. glass test tube. The liquid polymers, PEG and P(EO-PO), were added next and the components were blended thoroughly for several minutes using a glass rod. The DMSO was added last. Then the test tube was placed in an ice-water bath and the mixture was blended for several minutes. Preparations containing DMSO were blended on ice in order to deactivate the DMSO and avoid any premature gelation reactions. This assured that a proper dispersion of the components was achieved.

The test tube was then sealed and kept in a warm water bath around 40° C. for 30 minutes. The blends were left in closed containers at room temperature until dissolution tests were conducted. Mixtures which were allowed to gel for over 24 hours were opened once or twice a day and blended for several minutes. Samples of approximately 1 gram were cut from the gel and loaded into gelatin capsules for dissolution testing.

Recipes for the drug-loaded gels will be given in Example 1. The notation H/G/C/D will be used throughout the discussion to represent the gel composition as the percent by weight of PHEMA, PEG, P(EO-PO) and DMSO, respectively.

Dissolution Testing Procedure

The apparatus which was designed for the dissolution testing of the DTZ-loaded gels included a 4-neck, 500-mL, round-bottom flask which served as the dissolution vessel. It contained 400 mL of the release medium, a saline solution, pH 7.4 buffer solution. A polyethylene liner having a thickness of 1 mm and mesh size of 2 mm was used to make a 3-sided container for the capsule. The container was completely submerged in the solution to approximately 4 cm from the bottom of the flask and was held with copper wire from the central neck of the flask. The sample was confined vertically in the basket until the outer capsule dissolved. A 25-mL buret was attached to one of the side necks to hold reserve buffer solution. The flask was immersed in a 10×19 cm crystallizing dish filled with tap water so that the level of the buffer solution fell below that of the water bath. The entire apparatus was placed on a ceramic-top stirring hot plate. The hot plate was attached to an Omega® CN 9000 Series Microprocessor temperature controller. A temperature sensor connected to the controller was immersed in the release medium through a second side neck. After a five-hour stabilization period, the controller maintained the solution temperature at 37.0±0.2° C. This temperature is approximately that of the human body. Stirring bars of 1 and 2-in. lengths were used to stir the dissolution medium and the water bath simultaneously. The third neck served as the sampling portal and was stoppered to avoid evaporation.

Three-milliliter samples were taken from the solution at designated times during the experiment and stored in small vials. These were immediately replaced by equal volumes of fresh buffer solution. Dissolution of the drug device was carried out for eight hours. Samples were diluted accordingly with pH 7.4 buffer solution for subsequent assay and kept refrigerated.

Upon completion of the experiment, the swollen gels were removed from the basket, and the solvent was allowed to evaporate at room temperature and pressure. The final dry weights of the samples were recorded.

Kinetics of Drug Release a. Determination of Dialtiazem Hydrochloride Release by UV-VIS A Hewlett-Packard 8451-A Diode Array Spectrophotometer was used to measure UV absorption of the DTZ solutions taken during the experiments. Standards of known DTZ concentration were prepared for calibration and samples were diluted such that the measured absorbance fell within the linear range from 0.0 to 1.0. Calibration data were obtained for each set of assays. Two quartz glass Suprasil I cells with a 10-mm light path were used for UV measurements. DTZ absorption was quantified at 237 nm, the maximum of the absorption peak. For DTZ standard solutions, the absorbance increased linearly with concentration; therefore, the absorbance measured for the samples was easily converted to concentration. (The release index was calculated for the dialtiazem hydrochloride using a Hewlett-Packard Spectrophotometer to measure UV absorption of the DTZ solutions during the experiments and calculating a test fit time through a plot of the natural logarithm of the mass of the drug released at the time over the total mass of the drug in the matrix.)

Miscibility of Binary and Ternary Blends a. Determination of Thermal Properties by DSC Polymer blends containing PHEMA and PEG, two hydrophilic macromolecules, and P(EO-PO), a copolymer with a hydrophobic block linking the two hydrophilic blocks, were studied as controlled-release matrices. DTZ was selected as the water-soluble drug for immobilization in the gels. Drug release profiles were obtained for blends of various compositions to study the effect of the matrix components on the rate of DTZ release. The swelling characteristics of non-drug loaded gels were analyzed and the thermal properties of the unswollen gels were measured using DSC.

A Du Pont 9900 computer/thermal analyzer system with a Model 910 Differential Scanning Calorimeter (DSC) cell was used to investigate the miscibility in polymer blends and to measure glass transition and melting temperatures for the matrix polymers. Samples were sealed in aluminum DSC pans and cooled in the DSC cell using liquid nitrogen. DSC scans were obtained upon heating of the samples at a rate of 10° C./min with a nitrogen purge of 40 mL/min.

A 14.6-mg sample of PHEMA was analyzed by DSC from 0° C. to 120° C. DSC scans were carried out for samples of pure PEG (8.4 mg) and P(EO-PO) (6.8 mg) over the temperature range of −100° C. to 40° C.

Binary and ternary blends consisting of PHEMA, PEG and P(EO-PO) were prepared without DTZ loading for thermal analysis. The composition of these blends will be described by their weight percent of polymer. For example, the notation H50/G30/C20 will denote a blend having 50 percent PHEMA, 30 percent PEG, and 20 percent of the copolymer P(EO-PO). H/G/C will denote a ternary blend prepared with equal fractions of each polymer.

EXAMPLES 1–6

As Examples 1–3, binary blends H50/G50, H50/C50, and G50/C50 were examples prepared by adding approximately 0.5 g of each appropriate polymer to 3-mL vials. H50/G50 was combined with a metal stirring rod because of the mixture's high viscosity. It formed an extremely tacky, clear gel. Once the mixture reached a homogeneous consistency with no visible phase separation, a 24.3-mg sample was scanned from −100° C. to 100° C. H50/C50 was prepared in the same fashion. The mixture formed a translucent, viscous suspension of PHEMA particles in P(EO-PO). A 20.6-mg sample of the slurry was scanned from −100° C. to 100° C. G50/C50 was blended for several minutes and 5.5 mg of the clear solution was analyzed over the range −100° C. to 40° C.

DSC scans of ternary blends were conducted by cooling the samples to −100° C. then monitoring the heat flow up to 100° C. As Examples 4 and 5, two blends having the composition H/G/C were prepared by measuring equal amounts of each polymer into a 1-oz. glass bottle and a 4-in. test tube. The mixtures were stirred with a glass rod for 5 minutes and the containers sealed. After 10 days, the disc which had formed in the bottle was removed. An 8.0-mg sample was cut from the disc and blotted on filter paper to remove the excess liquid polymer which had phase-separated. The second of the two H/G/C blends was analyzed over several days. First, 23.5 mg was removed from the mixture soon after blending. Upon standing, the slurry which was formed during blending had phase-separated. It was stored at room temperature in a sealed test tube and periodically blended. After 3 and 6 days, samples of 18.1 mg and 12.3 mg, respectively, were cut from the gelled portion of the blend and sealed in DSC pans.

As Example 6, H50/G25/C25 was prepared by measuring the components into a 4-in. test tube, blending for 5 minutes, and allowing the mixture to gel at room temperature for 3 days with periodic mixing. A sample of 18.8 mg was then analyzed.

EXAMPLES 7–14

Swelling Studies

Swelling studies were conducted to determine equilibrium water content and percent weight loss. The percent swelling of PHEMA was determined at three temperatures. In Example 7, approximately 0.2 g of PHEMA were swollen in distilled water. The system was cooled to 0° C. in an ice-water bath. The gel was removed after 20 minutes, blotted on filter paper and weighed. This was repeated until an equilibrium weight was observed. The equilibrium water content was calculated by the following equation:

$$ewc = \frac{[\text{wt. (hydrated gel)} - \text{wt. (dehydrated gel)}] * 100\%}{\text{wt. (hydrated gel)}} \quad (6)$$

Next, for Examples 8 and 9, the same procedure was followed for PHEMA swollen at room temperature and 60° C.

In Examples 10 and 11, H50/G50 and H50/C50 blends were swollen in 50 mL of pH 7.4 buffer solution. The weights of the swollen gels were recorded periodically over a two-month period. After 15 days of swelling, the solvent was poured off and replaced with fresh buffer solution. After 25 days, the solvent was poured off and replaced with distilled water. The gels were finally placed on petri dishes in a desiccator. The dry weights were recorded and the percent weight loss calculated.

In Example 12, the weight loss due to swelling of a H50/G25/C25 blend prepared as set forth in Example 6 was observed by placing approximately 0.43 g of the blend in 40 mL of pH 7.4 buffer solution. The system was maintained at room temperature. The percent water content was determined daily until an equilibrium was achieved. The solution was replaced one time, but this did not cause a change in equilibrium swelling. The gel was dried in a desiccator, and the final dry weight was recorded.

For Examples 13 and 14, blends of H50/G30/C20 and H50/G40/C10, each having a total weight of 1 g, were prepared in 4-in. test tubes, stoppered, and stored at room temperature for 3 days. The tubes were then filled with buffer solution to loosen the gel from the glass and transferred to beakers filled with more buffer solution. The gels were swollen with occasional stirring for 8 hours, and the percent swelling was determined. The solvent was evaporated from the gels by placing them in a desiccator for several days. Once dry, the percent weight loss due to swelling was calculated.

EXAMPLES 15 AND 16

UV-ViS Measurements of Gel Components

Molecules containing $\pi$ or non-bonding (n) electrons are capable of absorbing radiation in the ultraviolet region. The amount of radiation absorbed is equal to the energy required for the ground to excited state transition ($\pi \rightarrow \pi^*$ or $n-\pi^*$). The absorbing species or chromophore is stabilized in the excited state by conjugation in the molecule. The more extended the conjugation, the lower the energy required for the ground to excited state transition. As a result, highly conjugated molecules absorb radiation of longer wavelengths. For samples obeying Beer's Law, the absorbance increases linearly with concentration.

In Example 15, an absorption spectrum was prepared for the drug solution DTZ. The values for the absorbance of DTZ were taken as the maximum of its second peak which occurred at 237 nm. The absorbance of the first peak appeared to be caused not only by DTZ, but also by other components in the gel.

In Example 16, an absorption spectrum was prepared of the release medium from the dissolution of H35/G40/C25. The sample was taken after 30 minutes of dissolution. Comparison of the spectrum of Examples 15 and 16 suggests that DTZ may not be the only material leaching out from the gel upon swelling. The absorbencies at 237 nm were nearly identical, whereas the intensity of the first peak was greater for the drug-loaded gel than the pure drug. Also, the maximum absorbance was slightly shifted to lower wavelengths. Thus, it was determined that the measurement of DTZ absorption at 237 nm was not affected by the absorption of polymers which have diffused from the gel and into the release medium.

The blend H/G/C having equal parts of each component was swollen for 6 hours in pH 7.4 buffer solution and the spectrum of the solution upon removal of the hydrogel was taken. The maximum of the absorbance peak occurred at 206 nm. The diffusion of some low molecular weight materials from the gel upon swelling may have created the large change in absorbance at the lower wavelength.

The absorption spectrum for DMSO was also taken. The maximum absorbance occurred at 212 nm, identical to the wavelength at which the first spectra for DTZ occurred. A solution of an unloaded gelatin capsule was assayed and found to absorb radiation in this region as well.

EXAMPLES 17 AND 18

Drug Release Profiles

Effect of Gelation Time

Sufficient blending of the drug-loaded gels was found to be important in order to obtain adequate dispersion of the components in the mixture since proper dispersion allows for stronger and more interactions among the polymer chains. Hydrogen bonding is the specific intermolecular interaction responsible for miscibility in oxygen-containing polymers.

Among the materials used to prepare the gels for this study, PHEMA and PEG are the most hydrophilic. Hydrophilic sites exist in each repeat unit of these polymers, that is, in the side chains of PHEMA and along the backbone of PEG. These also serve as sites for water binding during swelling. The hydroxy groups at the chain ends of PEG and P(EO-PO), or at each side chain of PHEMA, can form hydrogen bonds with the ether oxygens in the PEG and P(EO-PO) backbones. The abundance of hydrogen-donating groups in the gel polymers makes them a good target for DMSO, a polar, aprotic solvent and hydrogen bond acceptor.

In Example 17, the blend H35/G50/D10 was prepared with DTZ and samples of the gel were cut and placed into gelatin capsules. The first sample from the gel was taken immediately and its drug release analyzed. Subsequent samples were analyzed after 1, 2, 3, and 20 days. The percents of drug released as a function of time from the gels are combined in FIG. 1. After eight hours of swelling in pH 7.4 buffer solution, the sample at 20 days released the highest amount of DTZ. The equilibrium values for all other samples were roughly similar. This result may be caused by the difference in the amount of drug loaded. The sample at 20 days contained 35 mg of DTZ whereas the other samples contained between 127 and 141 mg.

A trend in the initial release of drug from the gels was evident. FIG. 2 focusses on the first two hours of the release profiles in FIG. 1. It appeared that most of the drug was released during this time and the equilibrium was achieved after two hours. The first sample displayed the initial burst, common in many drug delivery systems. Over 30 percent of the drug was released within the first several minutes of swelling. By storing the gels for longer periods of time, there was a decrease in the rate at which drug was initially diffused from the gel. It was concluded that a waiting period of 3 days following blending was sufficient to sustain the initial burst of drug.

After the polymers were blended, the extent of intermolecular interactions appeared to be limited, judging from the separation between the PHEMA crystals and the liquid phase. Upon swelling, more of the free or non-hydrogen bonded chains could diffuse from the gel; the matrix started to degrade at a much faster rate. With longer gelation times, the interactions between the liquid-phase polymers and the solid PHEMA were enhanced, as evidenced by gel formation. The initially phase-separated liquid was gradually incorporated into the gel. The liquid phase acted as a plasticizer for PHEMA. Its solvating effect led to the transformation of PHEMA from the glassy to the rubbery state.

For the sample which was taken and swollen immediately after blending, the low value of the equilibrium fractional release may have been caused by the entrapment of DTZ within chain entanglements in the gel. This would suppress the mobility of the drug molecules. The change in release behavior of H35/G50/C5/D10 tends to suggest that the distribution of drug and the extent of intermolecular interactions within the gel vary over time.

The release indices for H35/G50/C5/D10 are listed in Table I below. The values for "n" were determined from the initial linear region of the $\ln(M_t/M_\infty)$ vs. $\ln(t)$ plots. The values for "t" represent the length of time for which this linearity occurred in the plot. In other words, the release index was determined as the slope of the $\ln(M_t/M_\infty)$ vs. $\ln(t)$ plots for the data shown in FIG. 6, but excluding the points after which equilibrium was reached.

TABLE I

Release Indices for the Diffusion of DTZ from H35/G50/C5/D10

| Gelation Time (days) | n | t(min) |
| --- | --- | --- |
| 1 | 0.644 | 40 |
| 2 | 0.914 | 75 |
| 3 | 1.08 | 90 |
| 20 | 0.969 | 60 |

The results show that over the first 3 days, the release index approached a value of 1. The length of time which it took to reach equilibrium increased with gelation time. Thus, by allowing more time for the blend to equilibrate, there was not only an extension in the release period, but also a change in the kinetics of drug release toward that of Case II transport. After 20 days, the release index did not change very much, but there was a decrease in the time to reach equilibrium.

In Example 18, the effect of gelation time was examined for a similar composition, H35/G50/C15, in which DMSO was eliminated. The gelation period over which the drug release was examined was extended to 6 weeks. FIG. 3 shows the release behavior from three samples. The gel swollen after 3 days released DTZ much faster than those gels swollen after 2 and 6 weeks. This was evident from the slopes of the initial linear regions of the release profiles. The sample run after 14 days produced the longest delay during the first two hours of dissolution. After two hours, the percent released remained fairly constant. In this time, the maximum percent released from the samples increased with increasing gelation time. These results seem to agree with those observed for H35/G50/C5/D10 discussed previously. The release indices were calculated for the 14-day and 42-day samples over the entire 8 hours of dissolution. (These were found to be n=0.806 and n=0.613, respectively. Both of these values suggest anomalous diffusion behavior for H35/G50/C15; however, the release from the 42-day sample appeared to be governed more by Fickian diffusion.)

EXAMPLES 19–23

Effect of Copolymer Content

In Examples 19–23, the effect of a blended copolymer was studied. P(EO-PO) was the only polymer in the matrix containing hydrophobic groups in its structure. The central PPO block comprised approximately 55 percent of the polymer by weight. The hydrophobicity in P(EO-PO) hinders interactions with other hydrophilic polymers and with water. It was expected that with a greater amount of hydrophobicity in the gel structure, the percent swelling and thus the amount of drug released would decrease.

The effect of P(EO-PO) on the release kinetics was examined by monitoring the drug release from five different blend compositions. The amount of P(EO-PO) ranged from 5 percent to 55 percent. The increase in the copolymer content was compensated by a decrease in the amount of PEG in the composition. Therefore, the weight percents of PHEMA and DMSO remained fixed at 35 percent and 10 percent, respectively. FIGS. 4–6 illustrate the release profiles for gels with varying P(EO-PO) content. A comparison of the equilibrium fractional release values can be made from FIG. 4. It appeared that low amounts of P(EO-PO) in the blend, i.e. from 5 to 15 weight percent, showed little variance in the maximum percent released. For the 15 weight percent sample there was a depression in the percent DTZ released evident around the time t=2h for this sample. An increase in P(EO-PO) to 20 percent produced a notable increase in the fractional release during the second half of the dissolution experiment.

With 55 percent P(EO-PO) in the gel, the matrix became more resistant to swelling due to its increased hydrophobic content. Consequently, the maximum percent released was found to decrease. The extent of swelling is not only a factor of hydrophobicity, but also of temperature. The interactions of both ethylene oxide and propylene oxide with water became less favorable with increasing temperature. Another factor which should be considered is the micellization behavior of P(EO-PO). Drug molecules may become trapped within the hydrophobic core of the micellar aggregates formed in aqueous solution.

The determination that the release behavior goes through a maximum with increasing P(EO-PO) content is shown more clearly by FIGS. 5 and 6. These plots focus on the first hour of dissolution during which time most of the drug was released from the gels. The trend shown by FIG. 5 suggests that by increasing the copolymer content up to 15 weight percent, the rate of drug release decreased. The reverse was true when the amount of copolymer was further increased from 15 percent up to 55 percent. This is illustrated in FIG. 6. The results indicated that for P(EO-PO) less than and greater than approximately 15 percent, the drug release occurred at a faster rate. The change in release behavior between the compositions having from 5 to 15 percent P(EO-PO) seemed larger than that for the decrease from 55 to 15 percent. Another factor which needs to be considered is that the amount of PEG is also changing. It can also be said that the drug release was more controlled when the amount of PEG dropped from 50 to 40 weight percent. Thus, the preferable range of copolymer is from about 5 to about 30 percent, with a more preferred range of from about 10 to about 20 percent. The similarity in the chemical structures of PEG and P(EO-PO) tends to suggest that these polymers are compatible with one another. The compatibility and interactions of each polymer with PHEMA seemed to be affected by swelling, judging from the behavior of the limiting compositions in the series.

The optimum P(EO-PO) content of 15 weight percent was further justified after the determination of the release indices for these samples. Table II lists the length of time that the drug release profile followed zero-order kinetics. These were determined from the $\ln(M_t/M_\infty)$ vs. $\ln(t)$ plots as the length of time for which the slope of the best fit line and the correlation coefficient ($R^2$) were closest to a value of 1.

TABLE II

Duration of Zero-Order DTZ Release from Blends Having Different C/G Ratios and 35% PHEMA, 10% DMSO

| Example # | Wt. % C | Wt. % G | t(h) | n |
|---|---|---|---|---|
| 19 | 5 | 50 | 1 | 1.02 |
| 20 | 10 | 45 | 1 | >>1 |
| 21 | 15 | 40 | 4 | 1.01 |
| 22 | 20 | 35 | 2 | 1.00 |
| 23 | 55 | 0 | 1.5 | 1.01 |

The time for which zero-order release was observed went through a maximum at 15 weight percent P(EO-PO), corresponding to the blend H35/G40/C15/D10. The duration of zero-order release increased from 1 to 4 hours with only a 10 percent increase in the amount of copolymer. For blends containing greater than 15 percent copolymer, the decrease in the zero-order interval was much more gradual, from 4 to 1.5 hours with a 40 percent increase in P(EO-PO).

EXAMPLES 24–26

Effect of DMSO

In Examples 24–26, the effect of DMSO was studied. DMSO is currently banned for use in pharmaceutical preparations. One of the objectives of this invention was to eliminate DMSO, if possible.

The release profiles for 3 different blend compositions containing 0, 10, and 20 weight percent DMSO are combined in FIG. 7. The results showed very small deviations in percent DTZ released over 8 hours. Data obtained for the first two hours of dissolution seemed to exhibit reproducible behavior regardless of the DMSO content. The 2-hour release index was n=1 for the blends containing 0 and 10 percent DMSO. The corresponding correlation coefficients were 0.971 and 0.969. The 2-hour release index for the blend prepared with 20 percent DMSO was much greater than 1. One possible explanation for this discrepancy is the correlation of the $\ln(M_t/M_\infty)$ data with ln(t). The value of the correlation coefficient was $R^2$=0.912. Between 2 and 8 hours, there was a modest difference in the percent DTZ released for H35/G35/C20/D10 with respect to the other two compositions. Each of the gels released approximately 70 percent of the initial DTZ loaded.

The 8-hour release indices were determined for the blends as well as the correlation coefficients of the best line fit to $\ln(M_t/M_\infty)$ vs. ln(t). The values of n and $R^2$ are similar for the blends H35/G40/C25 and H35/G35/C20/D10. Again, the discrepancy in n for H35/G20/C25/D20 seems to be the result of a poor correlation coefficient ($r^2$=0.827). The results are summarized in Table III.

TABLE III

Comparison of the 8-Hour Release Index and the Correlation Coefficient with the Wt. % DMSO in the Blend

| Example # | Blend Composition | n | $r^2$ |
|---|---|---|---|
| 24 | H35/G40/C25 | 0.730 | 0.909 |
| 25 | H35/G35/C20/D10 | 0.696 | 0.897 |
| 26 | H35/G20/C25/D20 | 0.977 | 0.827 |

The results suggest that the addition of DMSO to the blend does not create a pronounced change in the blend's drug release behavior which shows that the use of DMSO may be omitted.

EXAMPLES 27–29

Effect of PHEMA

In Examples 27 and 28, two sets of blends were prepared having the compositions H35/G40/C15/D10 and H35/G35/C20/D10. Within each set, the first gel was made using large crystals of PHEMA (c-PHEMA) and the second was made using PHEMA in the powder form (p-PHEMA). The results of the dissolution experiments are illustrated in FIGS. 8 and 9. For the blend H35/G40/C15/D10 shown in FIG. 8, the two matrices displayed identical release behavior during the first hour of dissolution, releasing DTZ at approximately the same rate. Between 1 and 4 hours, the gel prepared with c-PHEMA suppressed the drug release further than the gel containing p-PHEMA. The maximum DTZ released was increased 8 percent by decreasing the particle size of PHEMA.

Large PHEMA particles act as a barrier to the diffusion of DTZ. Upon swelling, the particles could absorb DTZ that may be dissolved in the surrounding solution. It is likely that this extensively hydrogen-bound material imbibes not only the release medium during swelling but also the drug solution located in the swollen portions of the gel. The smaller particle size PHEMA provides a larger surface area for interaction with PEG and P(EO-PO). It is also less of a barrier to diffusing molecules.

For the H35/G35/C20/D10 blend shown in FIG. 9, the two matrices seemed to release DTZ at somewhat different rates during the first few hours of dissolution. Between 3 and 6 hours, the percent DTZ released leveled off at nearly the same value for both samples. During the last two hours of dissolution, however, the percent release from the gel prepared with p-PEMA jumped to 80 percent whereas that for the gel having c-PHEMA remained constant at 70 percent. This late burst of drug following the equilibration period was believed to be a result of the network falling apart. It is important to note that the maximum percent of DTZ released after swelling for 8 hours was increased when p-PHEMA was substituted for c-PHEMA.

In Example 29, the release of DTZ from H60/G40 was examined. The results are shown in FIGS. 10 and 11. After 8 hours of swelling, only 41 percent of the DTZ was released. The fractional release did not appear to equilibrate at any particular time. This behavior tends to suggest that by increasing the amount of PHEMA in the blend composition, the rate of drug release can be controlled over a longer period of time.

It appears that with H60/G40, the release period could be extended beyond 8 hours since an equilibrium was not reached. With the increase in PHEMA, the rate and extent of swelling in the gel appear to have been reduced. Another factor is the increase in the glass transition temperature as the weight percent of PHEMA increases. Materials having high values of $T_g$ will exhibit very different swelling characteristics. The rate at which solvent diffuses into and swells the system is slower in glassy materials, or high $T_g$, materials.

The release index for the system was determined from the slope of the line of a plot and had a value of n =0.631. This value indicates that DTZ was released by the anomalous diffusion mechanism.

EXAMPLES 30-33

Reproducibility and Error Analysis of Release Profiles

When polymers of varying structures and molecular weights are combined in an attempt to form a homogeneous blend or crosslinked network, a uniform dispersion of the components is vital. This facilitates an adequate determination of the material's physical properties and the generation of reproducible results. Factors such as blending procedure, polymer miscibility, and phase separation can alter the swelling properties of and subsequent drug release from polymer blends.

In Examples 30–33, four separate blends all having the composition H35/G40/C25 were prepared and swollen for 8 hours at pH 7.4. Table IV summarizes the release indices calculated for gels swollen at 3, 10, and 42 days after blending. For day 3, the release profiles were further analyzed for n at 2 and 4 hours of dissolution. The mean values for n and their uncertainties are listed at the end of each column.

There appeared to be small deviations in the 8-hour release indices for blends swollen on day 3. The mechanism of solute transport seemed to shift from near zero-order to anomalous diffusion. H35/G40/C25 gave zero-order release of DTZ for approximately the first two hours and then followed the anomalous diffusion pattern.

Data obtained from the release experiments of sample 1 were analyzed to determine the error in the calculated fractional release and $\ln(M_t/M_\infty)$. The spectrophotometer readings for the absorbance of DTZ were given as the average of at least 7 measurements. Table V summarized the errors calculated for $M_t/M_\infty$ and $\ln(M_t/M_\infty)$ from the standard deviations of the absorbance, s(A). The three sets of data represent values determined throughout the 8-hour release experiments for H35/G40/C25 samples taken after 3, 10, and 42 days of gelation. The error in the absorbance which was computed by the instrument was less than roughly 0.01 absorbance units.

The standard deviation of the fractional release was calculated using the following equation:

$$s(M_t/M_\infty) = \frac{180.3952 * [m[s(A) + s(I)] + [s(m) * A/m^2]] * 100\%}{M_\infty} \quad (7)$$

The constant in Eq. 7 represents the molecular weight of DTZ multiplied by the volume of the release medium. The variables m and I are the slope and y-intercept of the calibration curve (Absorbance vs. Concentration of DTZ).

The deviations in $M_t/M_\infty$ were less than 0.2 percent, and those determined for $\ln(M_t/M_\infty)$ were less than 0.02. As a result, the errors in the x and y directions for the graphs of $M_t/M_\infty$ vs. Time and $\ln(M_t/M_\infty)$ vs. ln(t) are insignificant; therefore, error bars are not included in these figures.

TABLE IV

Release Indices the Diffusion of DTZ from H35/G40/C25 After 3, 10, and 42 days of Gelation

| Example # | Sample | n (3 days) t = 2 hrs | t = 4 hrs | t = 8 hrs | n (10 days) t = 8 hrs | n (42 days) t = 8 hrs |
|---|---|---|---|---|---|---|
| 30 | 1 | 1.030 | 0.877 | 0.730 | | |
| 31 | 2 | 0.948 | 0.819 | 0.692 | 1.020 | 0.705 |
| 32 | 3 | 0.898 | 0.855 | 0.772 | 0.720 | 0.536 |
| 33 | 4 | 0.947 | 0.793 | 0.607 | 0.709 | 0.830 |
|  | n | 0.956 | 0.836 | 0.700 | | |
|  |  | 0.055 | 0.037 | 0.070 | | |

Reproducibility was not achieved, however, over longer periods of time. The release index for day 10 varied from 0.7 to 1.0, and for day 42 it ranged from approximately 0.5 to 0.8.

The discrepancies in n for the last two columns of Table IV may have arisen from poor correlation between the $\ln(M_t/M_\infty)$ and ln(t) data or from changes within the matrix over time. During storage, phase separation occurred in some of the blends studied. A clear liquid layer formed over the gels. The physical nature of unloaded gels ranged from tacky and transparent to rubbery and translucent. It appeared that fractions of the liquid polymers interacted with PHEMA to form tough, rubbery materials. This can also be explained as a saturation of PHEMA with PEG and P(EO-PO) such that any excess polymer incapable of interacting with PHEMA diffused from the blend upon standing.

Different drug loadings ($M_\infty$) will have an effect on the release mechanism and maximum DTZ released. For example, the gels cut from sample 4 each contained 150±1 mg. Approximately 80 percent of the drug was released from the gels swollen after 3 and 10 days, but only 67 percent was released after 42 days. Another interesting trend observed for sample 4 was that the value for the 8-hour release index increased with time. In other words, the kinetics of the drug release showed a shift towards zero-order.

TABLE V

Error Analysis of the % DTZ Released and the $\ln(M_t/M_\infty)$ for H35/G40/C25

| A | s(A) | Mt/M∞ (%) | s(Mt/M∞) (%) | ln(Mt/M∞) | s(ln(Mt/M∞)) |
|---|---|---|---|---|---|
| 0.0785 | 0.0018 | 12.81 | 0.09 | 2.550 | 0.007 |
| 0.1197 | 0.0013 | 19.54 | 0.09 | 2.972 | 0.004 |
| 0.1518 | 0.0026 | 24.78 | 0.10 | 3.210 | 0.004 |
| 0.2021 | 0.0014 | 32.99 | 0.10 | 3.496 | 0.003 |
| 0.2382 | 0.0034 | 38.87 | 0.11 | 3.660 | 0.003 |
| 0.2734 | 0.0042 | 44.62 | 0.12 | 3.798 | 0.003 |
| 0.3115 | 0.0077 | 50.83 | 0.14 | 3.929 | 0.003 |
| 0.4128 | 0.0016 | 67.53 | 0.12 | 4.213 | 0.002 |
| 0.4552 | 0.0002 | 74.30 | 0.11 | 4.308 | 0.001 |
| 0.4953 | 0.0022 | 80.83 | 0.13 | 4.392 | 0.002 |
| 0.4945 | 0.0014 | 80.70 | 0.12 | 4.391 | 0.0001 |
| 0.4793 | 0.0012 | 78.23 | 0.12 | 4.360 | 0.0002 |
| 0.4946 | 0.0005 | 80.73 | 0.12 | 4.391 | 0.0001 |
| 0.0390 | 0.0024 | 6.40 | 0.09 | 1.856 | 0.014 |
| 0.0578 | 0.0026 | 9.48 | 0.09 | 2.249 | 0.009 |
| 0.0982 | 0.0060 | 16.11 | 0.11 | 2.780 | 0.007 |
| 0.1312 | 0.0006 | 21.53 | 0.09 | 3.070 | 0.004 |
| 0.1776 | 0.009 | 29.15 | 0.09 | 3.372 | 0.003 |
| 0.2346 | 0.0059 | 38.50 | 0.12 | 3.651 | 0.003 |
| 0.2928 | 0.0098 | 48.04 | 0.15 | 3.872 | 0.003 |
| 0.4082 | 0.0047 | 66.98 | 0.13 | 4.204 | 0.002 |
| 0.4531 | 0.0021 | 74.34 | 0.12 | 4.309 | 0.002 |
| 0.4613 | 0.0114 | 76.69 | 0.17 | 4.327 | 0.002 |
| 0.4507 | 0.0070 | 73.95 | 0.15 | 4.303 | 0.002 |
| 0.4804 | 0.0037 | 78.83 | 0.13 | 4.367 | 0.002 |
| 0.4875 | 0.0043 | 79.99 | 0.14 | 4.382 | 0.002 |
| 0.0241 | 0.0005 | 3.85 | 0.08 | 1.348 | 0.020 |
| 0.0367 | 0.0005 | 5.86 | 0.08 | 1.769 | 0.014 |
| 0.0585 | 0.0004 | 9.34 | 0.08 | 2.234 | 0.009 |
| 0.0900 | 0.0005 | 14.37 | 0.09 | 2.665 | 0.006 |
| 0.1375 | 0.0005 | 21.95 | 0.09 | 3.089 | 0.004 |
| 0.2836 | 0.0006 | 45.28 | 0.10 | 3.813 | 0.002 |
| 0.3703 | 0.0006 | 59.11 | 0.11 | 4.079 | 0.002 |
| 0.4005 | 0.0007 | 63.93 | 0.11 | 4.158 | 0.002 |
| 0.4117 | 0.0009 | 65.73 | 0.12 | 4.186 | 0.002 |
| 0.4105 | 0.0007 | 65.52 | 0.12 | 4.186 | 0.002 |
| 0.4142 | 0.0008 | 66.13 | 0.12 | 4.192 | 0.002 |
| 0.4175 | 0.0009 | 66.65 | 0.12 | 4.199 | 0.002 |

Swelling Behavior of Hydrogels

Hydrogels are capable of absorbing very large amounts of water. The extent of swelling is dependent on the gel's physical and chemical structure. PHEMA is a high molecular weight, water-swellable polymer. The swelling of PHEMA was analyzed at three different temperatures. It was found that as the temperature decreased, the percent swelling was increased. It has been suggested that the dehydration of a material at increased temperatures may result in a lower bound-water fraction. At room temperature, PHEMA gel was found to have an equilibrium water content of 38 percent.

Blends of PHEMA with each low molecular weight polymer were prepared and their swelling behavior in pH 7.4 buffer solution and in distilled water were analyzed. A 50/50 mixture of PHEMA and PEG formed a homogeneous gel that was transparent and extremely tacky. H50/G50 contained 66 percent water after one day of swelling at pH 7.4. A 50/50 mixture of PHEMA and P(EO-PO) formed a cloudy slurry that did not appear to have a homogeneous consistency. H50/C50 contained 45 percent water under the same conditions. Following 15 days of swelling, the water content of H50/G50 dropped, while that in H50/C50 increased. This seems to suggest that interactions between PHEMA and P(EO-PO) were enhanced for some time by swelling the slurry. The mixture did not dissolve or fall apart once placed in solution, but instead formed one continuous hydrogel. After 20 days, the percent swelling decreased in both blends. This was believed to be a result of diffusion of the water-soluble polymers from the matrix. As water penetrates into the gel, it dissolves PEG and P(EO-PO).

It is interesting to note that when the gels were transferred to plain distilled water, their water content increased tremendously even though some weight loss may have occurred. After 10 days of swelling in distilled water, the water content of H50/G50 decreased, suggesting further weight loss. The water content of H50/C50 remained relatively constant. It appeared that the dissolution and diffusion of PEG occurred at a much slower rate than P(EO-PO). The decrease in percent swelling was greater for H50/G50 and also greater when the blends were swollen in buffer solution. The diffusion of water-soluble polymers out of the blend was supported by the substantial loss in dry weight, 55 percent for the H50/G50 blend and 49 percent for the H50/C50 blend.

Ternary blends containing 50 weight percent PHEMA were analyzed for percent swelling and weight loss. After 8 hours of swelling H50/G30/C20 and H50/G40/C10 in pH 7.4 buffer solution, the gel containing a higher ratio of PEG to P(EO-PO) absorbed a greater amount of solution, but its dry weight loss was slightly less. Previous results for binary mixtures had shown that a larger amount of water diffused into H50/G50 within the first day of swelling.

The blend H50/G25/C25 absorbed its own weight in water after swelling at pH 7.4 for one week. The gel had a water content of 62 percent after the first day, and then showed a gradual decrease toward equilibrium. FIG. 26 illustrates the swelling behavior of H50/G25/C25. The dry weight loss for the blend was 38 percent. The weight loss due to swelling decreased by increasing the G/C ratio in the composition. This again suggests the greater tendency for P(EO-PO) to diffuse out from the system. Table VI summarizes the results from swelling and weight loss measurements.

TABLE VI

Water Content and Dry Weight Loss Due to Swelling for Mixtures of PHEMA with PEG and/or P(EO-PO)

| Blend Composition | Water Content (%) | Weight Loss (%) |
|---|---|---|
| H50/G50 | | 55 |
| Day 1 | 66 | |
| 15 | 47 | |
| 20 | 28 | |
| 25 | 22 | |
| 30 | 61 | |
| 35 | 47 | |
| 40 | 42 | |
| H50/C50 | | 49 |
| Day 1 | 45 | |
| 15 | 60 | |
| 20 | 44 | |
| 25 | 36 | |
| 30 | 77 | |
| 35 | 73 | |
| 40 | 73 | |
| H50/G40/C10 | 47 | 31 |
| H50/G30/C20 | 38 | 34 |
| H50/G25/C25 | 50 | 38 |

Determination of Thermal Properties by DSC

DSC diagrams were obtained for each pure polymer.

The copolymer P(EO-PO) exhibited a glass transition around −67° C. and an endothermic melting peak at approximately 21° C. upon heating. It has previously been measured in the range from −65° to −72° C. with an ethylene oxide content between 18 and 81 percent.

Blending equal portions of PHEMA, PEG and P(EO-PO) produced a translucent, rubbery gel with some phase-separation of the liquid polymer. A sample of the gel was blotted on filter paper to remove the excess liquid from the surface and then analyzed using DSC. The gelled portion of this blend gave a single glass transition temperature at around −51° C. The $T_g$ occurred at the same temperature as that for H50/G50. This tends to suggest that the liquid layer which had phase-separated was predominantly P(EO-PO).

A second blend of the same composition, H/G/C, was analyzed over a one-week period in order to examine the interactions among the polymers more closely. DSC measurements were first conducted on a sample immediately after blending. This sample was denoted H/G/C (1). The diagram showed transitions for $T_g$ at −64° C. and $T_m$ at 16° C. Upon storing the blend at room temperature for three days, a second DSC scan was obtained. The glass transition had shifted to −52° C. and the melting peak appeared at 18° C. There was little change in the transitions observed for the mixture following 6 days of storage. The shift in Tg for the ternary blend towards that for the binary blend H50/G50 indicated the outward diffusion and phase separation of P(EO-PO) from the gel. Also, the characteristic temperature of the melting peak increased gradually with time toward that for pure P(EO-PO).

The DSC spectrum was taken for H50/G25/C25. With an increase in PHEMA from 33 percent for H/G/C to 50 percent, the glass transition temperature was moderately increased to −47° C. However, there was no significant change in the $T_g$ detected for P(EO-PO). Table VII summarizes the results obtained from DSC thermograms.

TABLE VII

DSC Results of the Glass Transition and Melting Temperatures for the Pure Components and Their Blends

| Composition | Tg (°C.) | Tm (°C.) |
|---|---|---|
| PHEMA | 70 | |
| PEG | | 5 |
| P(EO-PO) | −67 | 21 |
| H50/G50 | −51 | |
| H50/C50 | −66 | 18 |
| G50/C50 | −66 | 18 |
| H/G/C | −51 | |
| H/G/C (1) | −64 | 16 |
| H/G/C (3) | −52 | 18 |
| H/G/C (6) | −50 | 19 |
| H50/G25/C25 | −47 | 17 |

While in accordance with the patent statutes the best mode and preferred embodiment has been set forth, the scope of the invention is not limited thereto, but rather by the scope of the attached claims.

What is claimed is:

1. A controlled-release composition comprising:
  an active ingredient dispersed in a matrix, said matrix comprising a blend of
  a) a hydrophilic polyhydroxyalkyl acrylate or methacrylate,
  b) a polyalkylene glycol; and
  c) a time-release extending agent which is a low molecular weight copolymer having a number average molecular weight from about 500 to about 10,000 and having both hydrophilic and hydrophobic groups.

2. A controlled-release composition as set forth in claim 1, wherein said hydrophilic polydroxyalkyl acrylate or methacrylate has the general formula I:

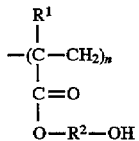

wherein $R^1$ is alkyl having 1–4 carbon atoms, and $R^2$ is alkyl having 1–8 carbon atoms.

3. A controlled-release composition as set forth in claim 2, wherein $R^1$ is alkyl having 1 or 2 carbon atoms and $R^2$ is alkyl having 1–4 carbon atoms.

4. A controlled-release composition as set forth in claim 3, wherein $R^1$ is methyl and $R^2$ is ethyl.

5. A controlled-release composition as set forth in claim 1, wherein the polyalkylene glycol is polyethylene glycol.

6. A controlled-release composition as set forth in claim 1, wherein the copolymer is a diblock or triblock copolymer which is the polymerization product of ethylene oxide and propylene oxide.

7. A controlled-release composition as set forth in claim 1, wherein the copolymer has one or more of the formula HO—(AB)—H, HO—(ABA)—H, or HO—(BAB)—H wherein A is (CH$_2$CH$_2$O) and B is (CH(CH$_3$)CH$_2$O).

8. A controlled-release composition as set forth in claim 7, wherein the copolymer has the formula III:

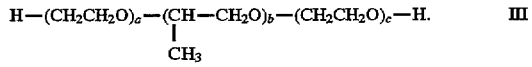

9. A controlled-release composition as set forth in claim 8, wherein the copolymer has a number average molecular weight of from about 1,000 to about 5,000.

10. A controlled-release composition as set forth in claim 9, wherein the copolymer has a number average molecular weight of from about 2,000 to about 4,000.

11. A controlled-release composition as set forth in claim 1, wherein the active ingredient is an agricultural or pharmaceutical agent.

12. A controlled-release composition as set forth in claim 11, wherein the active ingredient is dialtiazem hydrochloride.

13. A controlled-release composition comprising
  an active ingredient dispersed in a matrix which is a blend of
  a) from about 10 to about 90 percent of a polyhydroalkyl acrylate or methacrylate having a number average molecular weight of from about 500,000 to about 2,000,000 and having the general formula I

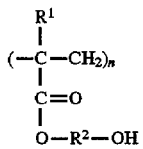

wherein $R^1$ is alkyl having 1–4 carbon atoms and $R^2$ is alkyl having 1–8 carbon atoms; and
  b) from about 5 to about 85 percent of a hydrophilic glycol having a number average molecular weight of from about 200 to about 1,000; and
  c) from about 5 to about 30 percent of a composition having a number average molecular weight of from about 500 to about 10,000, and being the polymerization product of ethylene oxide and propylene oxide; all percentages being based on the total weight of a+b+c.

14. A controlled-release composition as set forth in claim 1, wherein a) a poly(hydroxyethyl) methacrylate and b) is polyethylene.

15. A controlled-release composition as set forth in claim 14, wherein the poly(hydroxyethyl) methacrylate has a number average molecular weight of from about 750 to about 1,500,000; the polyethylene glycol has a number average molecular weight of from about 300 to about 600; and the poly(ethylene-oxide/propylene oxide) has a number average molecular weight of from about 1,000 to about 5,000 and is a diblock or a triblock copolymer.

16. A controlled-release composition as set forth in claim 15, wherein the poly(ethylene oxide-propylene oxide) is present at from about 10 to about 20 percent and has a number average molecular weight of from about 2,000 to about 4,000.

17. A controlled-release composition as set forth in claim 16, wherein the poly(ethylene oxide-propylene oxide) has a general formula III:

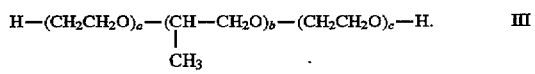

18. A controlled-release composition as set forth in claim 13, wherein the active ingredient is a pharmaceutical composition.

19. A composition for use as a controlled-release matrix comprising a blend of
  a) from about 30 to about 70 percent by weight (narrowest range) of poly(hydroethyl) methacrylate having a number average molecular weight of from about 750,000 to about 1,500,000;
  b) from about 20 to about 60 percent by weight (narrowest range) of polyethylene glycol having a number average molecular weight of from about 300 to about 500; and c) from about 10 to about 20 percent by weight (narrowest range) of the polymerization product of ethylene oxide and propylene oxide having a number average molecular weight of from about 2,000 to about 4,000, said percentages being based upon the total weight of a+b+c.

20. A composition for use as a controlled-release matrix according to claim 19, wherein the polymerization product of ethylene oxide and propylene oxide has a formula of HO—(AB)—H or HO—(ABA)—H or HO—(BAB)—H, wherein A is preferably ($CH_2CH_2O$) and B is preferably ($CH(CH_3)CH_2O$).

21. A composition for use as a controlled-release matrix according to claim 20, wherein the poly(ethylene oxide propylene oxide) has the formula III $$H-(CH_2CH_2O)_a-(CH(CH_3)-CH_2O)_b-(CH_2CH_2O)_c-H. \quad \text{III}$$

* * * * *